(12) United States Patent
Irie

(10) Patent No.: US 10,869,649 B2
(45) Date of Patent: Dec. 22, 2020

(54) ULTRASOUND TRANSDUCER MODULE AND ULTRASOUND ENDOSCOPE

(71) Applicant: OLYMPUS CORPORATION, Tokyo (JP)

(72) Inventor: Kei Irie, Akiruno (JP)

(73) Assignee: OLYMPUS CORPORATION, Tokyo (JP)

( * ) Notice: Subject to any disclaimer, the term of this patent is extended or adjusted under 35 U.S.C. 154(b) by 365 days.

(21) Appl. No.: 15/856,572

(22) Filed: Dec. 28, 2017

(65) Prior Publication Data

US 2018/0132820 A1 May 17, 2018

Related U.S. Application Data

(63) Continuation of application No. PCT/JP2016/069315, filed on Jun. 29, 2016.

(30) Foreign Application Priority Data

Jul. 13, 2015 (JP) .................................. 2015-139654

(51) Int. Cl.
*A61B 8/12* (2006.01)
*A61B 8/14* (2006.01)
*A61B 8/00* (2006.01)

(52) U.S. Cl.
CPC .................. *A61B 8/12* (2013.01); *A61B 8/14* (2013.01); *A61B 8/4483* (2013.01)

(58) Field of Classification Search
None
See application file for complete search history.

(56) References Cited

U.S. PATENT DOCUMENTS

2008/0089181 A1\* 4/2008 Adachi ................. B06B 1/0292
367/189
2013/0204140 A1\* 8/2013 Irie .......................... A61B 8/12
600/459
(Continued)

FOREIGN PATENT DOCUMENTS

EP 2 591 731 A1 5/2013
JP 2005130944 A 5/2005
(Continued)

OTHER PUBLICATIONS

Extended Supplementary European Search Report dated Feb. 28, 2019 in European Patent Application No. 16 82 4272.5.
(Continued)

*Primary Examiner* — Serkan Akar
*Assistant Examiner* — Jillian K. McGough
(74) *Attorney, Agent, or Firm* — Scully, Scott, Murphy & Presser, P.C.

(57) ABSTRACT

An ultrasound transducer module includes: an ultrasound transducer configured to transmit and receive ultrasound; a substrate electrically connected with the ultrasound transducer and including a first wiring pad at a portion different from a connection portion with the ultrasound transducer; and a casing that includes an accommodation hole for accommodating the ultrasound transducer and the substrate and that includes a holding hole continued to the accommodation hole and capable of holding a portion of the substrate, the casing having a plurality of electrode pads provided on an outer surface of the casing and having a plurality of second wiring pads provided in the holding hole, each second wiring pad being electrically connected with a corresponding electrode pad among the plurality of electrode pads, and electrically connected with the first wiring pad.

6 Claims, 6 Drawing Sheets

(56) References Cited

U.S. PATENT DOCUMENTS

2014/0046190 A1* 2/2014 Ogawa ................ A61B 8/4444
600/462
2015/0297807 A1* 10/2015 Leblanc ................ A61M 1/008
600/439

FOREIGN PATENT DOCUMENTS

| JP | 2005130945 A | 5/2005 |
| JP | 2009028109 A | 2/2009 |
| JP | 2014057136 A | 3/2014 |

OTHER PUBLICATIONS

International Search Report dated Aug. 30, 2016 issued in PCT/JP2016/069315.

* cited by examiner

ULTRASOUND TRANSDUCER MODULE AND ULTRASOUND ENDOSCOPE

CROSS-REFERENCE TO RELATED APPLICATIONS

This application is a continuation of PCT international application Ser. No. PCT/JP2016/069315 filed on Jun. 29, 2016 which designates the United States, incorporated herein by reference, and which claims the benefit of priority from Japanese Patent Application No. 2015-139654, filed on Jul. 13, 2015, incorporated herein by reference.

BACKGROUND

1. Technical Field

The disclosure relates to an ultrasound transducer module including an ultrasound transducer that transmits ultrasound to an observation target, receives an ultrasound echo reflected on the observation target and converts the ultrasound echo into an electrical signal, and relates to an ultrasound endoscope including the ultrasound transducer at a distal end of an insertion portion.

2. Related Art

Ultrasound is applied in some cases for observing a characteristic of a living tissue or a material as an observation target. Specifically, an ultrasound observation apparatus performs predetermined signal processing onto an ultrasound echo received from an ultrasound transducer configured to transmit and receive ultrasound, whereby information related to the characteristic of the observation target can be obtained.

The ultrasound transducer includes a plurality of piezoelectric elements that converts an electrical pulse signal into an ultrasound pulse (acoustic pulse), emits the ultrasound pulse to the observation target, and converts the ultrasound echo reflected on the observation target into an electrical echo signal, and outputs the echo signal. The ultrasound echo is obtained from the observation target, for example, by arranging the plurality of piezoelectric elements in a predetermined direction and electronically switching the elements related to transmission and reception.

There are a plurality of types of known ultrasound transducers having different transmission and reception directions of ultrasound beams, such as a convex type, a linear type, and a radial type. Among these, the convex type ultrasound transducer has a plurality of piezoelectric elements arranged along a curved surface, and each of the piezoelectric elements emits an ultrasound beam in a radial direction of the curved surface (refer to JP 2009-28109 A, for example).

FIG. 7 is a diagram schematically illustrating an exemplary configuration of a distal end portion of an ultrasound endoscope including a conventional convex type ultrasound transducer. FIG. 8 is a partial cross-sectional view corresponding to line B-B illustrated in FIG. 7, including a plane passing through a longitudinal axis N10 of the distal end portion as a cross-sectional plane. As illustrated in FIGS. 7 and 8, a conventional ultrasound transducer module 300 is constituted with a casing 302. The casing 302 includes an accommodation hole 302a and an insertion hole 302b. The accommodation hole 302a accommodates an ultrasound transducer 301 described below. A cable 311 connected to the ultrasound transducer 301 is inserted into the insertion hole 302b. The casing 302 includes the convex type ultrasound transducer 301 described above, a plurality of cables 311 and a relay substrate 312. Each of the plurality of cables 311 is electrically connected to each of the piezoelectric elements of the ultrasound transducer 301. The relay substrate 312 relays between the ultrasound transducer 301 and the plurality of cables 311. The ultrasound transducer 301 and the relay substrate 312 are accommodated in the accommodation hole 302a, and the plurality of cables 311 are inserted into the insertion hole 302b. The relay substrate 312 includes a rigid substrate 312a and a flexible substrate 312b. The rigid substrate 312a is connected to the ultrasound transducer 301. The flexible substrate 312b is connected to the rigid substrate 312a and connected with the plurality of cables 311.

FIG. 9 is a view illustrating a portion of a method for manufacturing an ultrasound endoscope including the conventional convex type ultrasound transducer, illustrating a method for arranging the ultrasound transducer in the casing of the ultrasound transducer module. The ultrasound transducer module 300 is manufactured by first bonding a connection section 3120 of the flexible substrate 312b, to which the plurality of cables 311 are connected, to the rigid substrate 312a attached to the ultrasound transducer 301 (refer to FIG. 8, for example), and thereafter, inserting the ultrasound transducer 301 into the accommodation hole 302a from the cable 311 side and bonding the ultrasound transducer 301 to the accommodation hole 302a, as illustrated in FIG. 9.

SUMMARY

In some embodiments, an ultrasound transducer module includes: an ultrasound transducer configured to transmit and receive ultrasound; a substrate electrically connected with the ultrasound transducer and including a first wiring pad at a portion different from a connection portion with the ultrasound transducer; and a casing that includes an accommodation hole for accommodating the ultrasound transducer and the substrate and that includes a holding hole continued to the accommodation hole and capable of holding a portion of the substrate, the casing having a plurality of electrode pads provided on an outer surface of the casing and having a plurality of second wiring pads provided in the holding hole, each second wiring pad being electrically connected with a corresponding electrode pad among the plurality of electrode pads, and electrically connected with the first wiring pad.

In some embodiments, an ultrasound endoscope includes: an insertion portion having a distal end with the ultrasound transducer module, the insertion portion being configured to be inserted into the subject; and a cable electrically connectable to the ultrasound transducer module.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
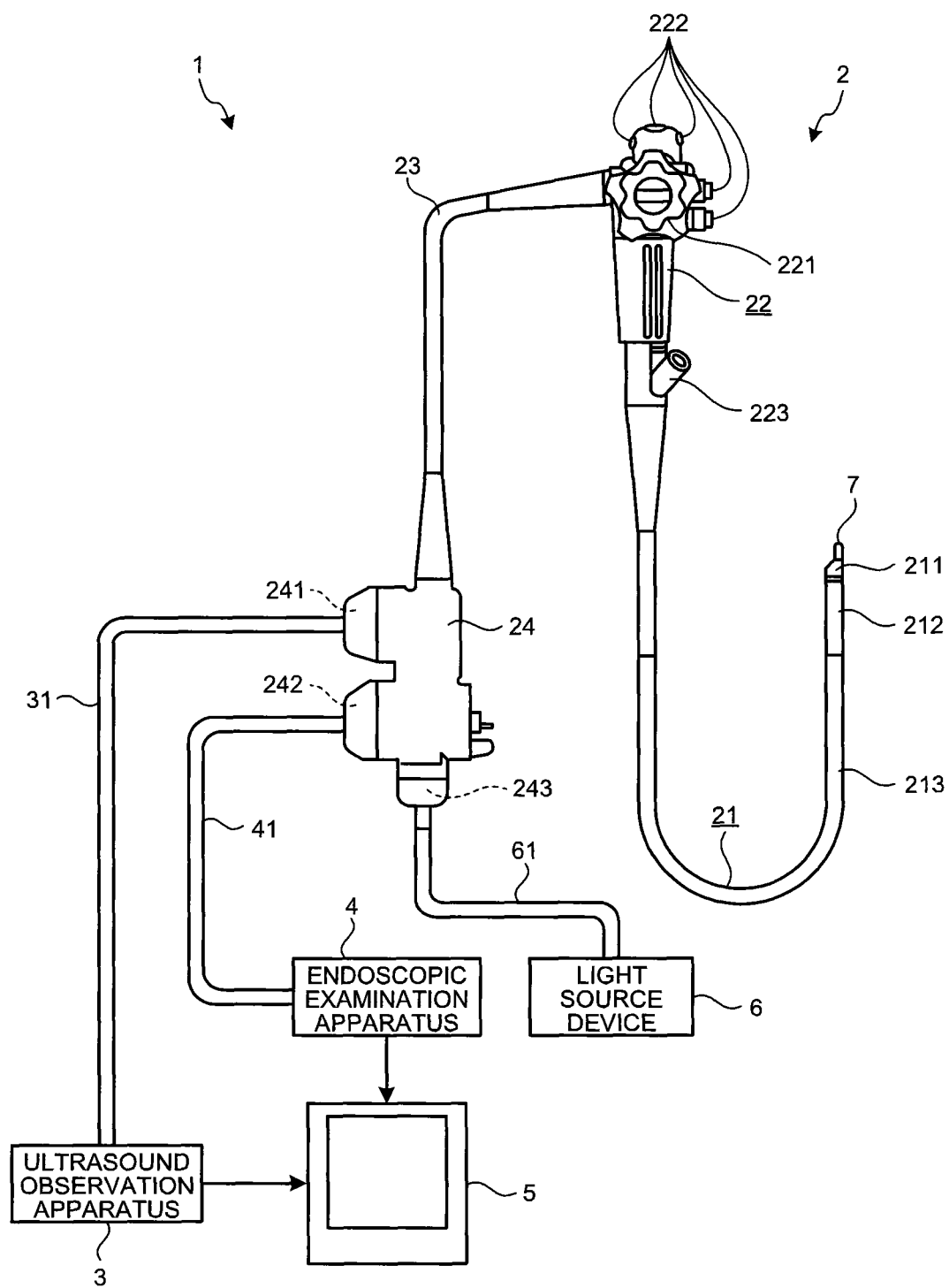
FIG. 1 is a diagram schematically illustrating an endoscope system according to a first embodiment of the disclosure.

Hereinafter, embodiments of the disclosure (hereinafter, referred to as embodiment(s)) will be described with reference to the drawings. Note that the disclosure is not limited by the following embodiments. In the drawings, same reference signs are attached to the same portions.

First Embodiment

FIG. 1 is a diagram schematically illustrating an endoscope system according to a first embodiment of the disclosure. An endoscope system 1 is a system for performing ultrasound diagnosis of internal portions of a subject such as a human using an ultrasound endoscope. As illustrated in FIG. 1, the endoscope system 1 includes an ultrasound endoscope 2, an ultrasound observation apparatus 3, an endoscopic examination apparatus 4, a display device 5, and a light source device 6.

The ultrasound endoscope 2 includes, on its distal end portion, an ultrasound transducer, thereby converting an electrical pulse signal received from the ultrasound observation apparatus 3 into an ultrasound pulse (acoustic pulse) and emits it to the subject. The ultrasound transducer also converts an ultrasound echo reflected on the subject into an electrical echo signal expressed by a voltage change and outputs the signal.

The ultrasound endoscope 2 typically includes imaging optics and imaging sensors. The ultrasound endoscope 2 can be inserted into gastrointestinal tracts (esophagus, stomach, duodenum, and large intestine) or respiratory organs (trachea, bronchus) of the subject and can capture the gastrointestinal tract and the respiratory organs. Moreover, it is possible to capture their surrounding organs (pancreas, gall bladder, bile duct, biliary tract, lymph nodes, mediastinal organs, blood vessels, or the like) using ultrasound. The ultrasound endoscope 2 includes a light guide that guides illumination light emitted to the subject at the time of optical imaging. The light guide is configured such that a distal end portion thereof reaches a distal end of an insertion portion of the ultrasound endoscope 2 into the subject, while a proximal end portion thereof is connected to the light source device 6 that generates illumination light.

As illustrated in FIG. 1, the ultrasound endoscope 2 includes an insertion portion 21, an operating portion 22, a universal cord 23, and a connector 24. The insertion portion 21 is a portion to be inserted into the subject. As illustrated in FIG. 1, the insertion portion 21 includes a distal end portion 211, a bending portion 212, and a flexible tube portion 213. The distal end portion 211 having rigidity is provided on a distal end side of the insertion portion 21 and holds an ultrasound transducer 7. The bending portion 212 is bendable and coupled to the proximal end side of the distal end portion 211. The flexible tube portion 213 has flexibility and is coupled to the proximal end side of the bending portion 212. While specific illustration is omitted herein, the insertion portion 21 internally includes a light guide, a plurality of signal cables, and a treatment instrument insertion passage. The light guide transmits illumination light supplied from the light source device 6. The plurality of signal cables transmits various signals. The treatment instrument insertion passage is used for inserting treatment instruments.

The ultrasound transducer 7 may be any of a convex type transducer and a linear type transducer. The first embodiment is described as a case where the ultrasound endoscope 2 includes a convex type ultrasound transducer, as the ultrasound transducers 7, that includes a plurality of piezoelectric elements in an array form and configured to perform electronic scan by electronically switching piezoelectric elements involved in transmission and reception, and delaying transmission and reception of each of the piezoelectric elements. The configuration of the ultrasound transducer 7 will be described below.

Figure 2:
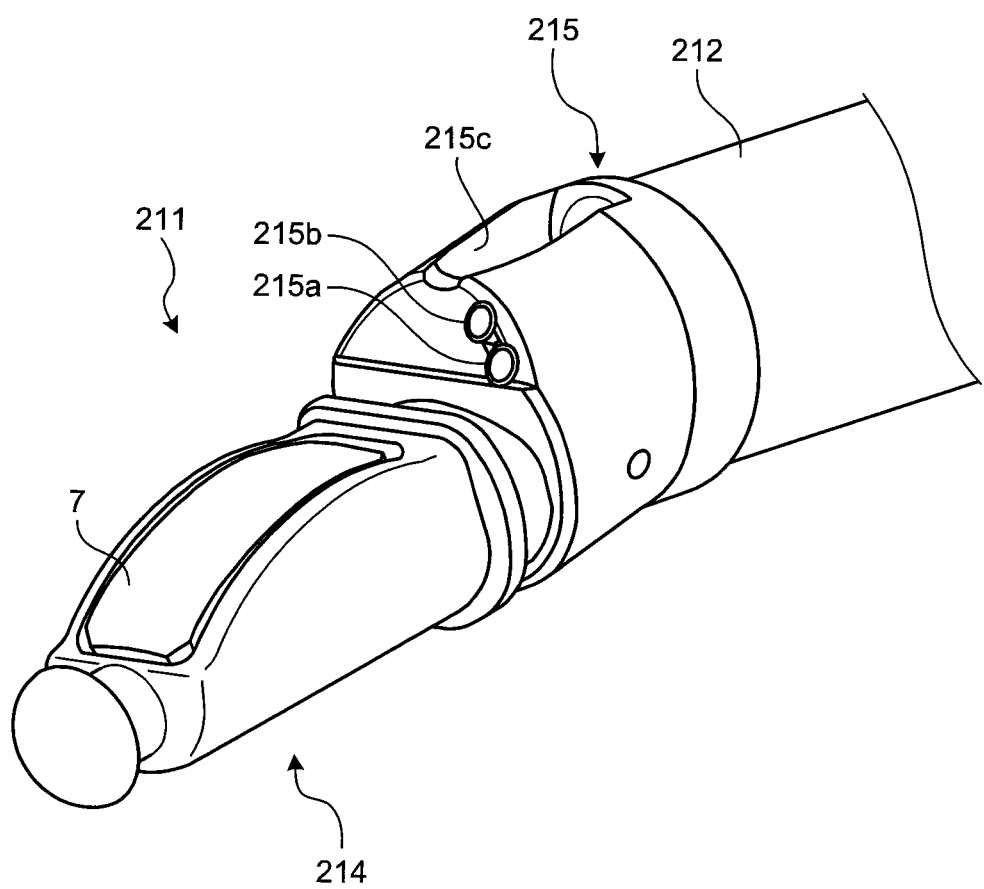
FIG. 2 is a perspective view schematically illustrating a configuration of a distal end of an insertion portion of an ultrasound endoscope according to the first embodiment of the disclosure.

FIG. 2 is a perspective view schematically illustrating a configuration of a distal end of the insertion portion of the ultrasound endoscope according to the first embodiment. As illustrated in FIG. 2, the distal end portion 211 includes an ultrasound transducer module 214 and an endoscope module 215. The ultrasound transducer module 214 holds the ultrasound transducer 7. The endoscope module 215 includes an illumination lens 215a and an objective lens 215b. The illumination lens 215a converges illumination light and emits the illumination light to the outside. The objective lens 215b is a portion of the imaging optical systems and takes in the light from the outside. The endoscope module 215 includes a treatment instrument protrusion port 215c that communicates with the treatment instrument insertion passage formed inside the insertion portion 21 and allows a treatment instrument to protrude from the distal end of the insertion portion 21. The treatment instrument insertion passage is arranged such that a portion around the end portion continued to the treatment instrument protrusion port 215c is inclined with respect to a longitudinal axis N (refer to FIG. 3) of the insertion portion 21 and that the treatment instrument protrudes from the treatment instrument protrusion port 215c in a direction inclined with respect to the longitudinal axis N. Herein, the longitudinal axis N is an axis along the longitudinal direction of the insertion portion 21. While the axial direction varies on the bending portion 212 and the flexible tube portion 213, depending on individual positions, the longitudinal axis N is an axis having a constant straight line on the distal end portion 211 having rigidity.

The operating portion 22 is coupled to the proximal end side of the insertion portion 21 and receives various types of operation from a doctor, or the like. As illustrated in FIG. 1, the operating portion 22 includes a bending knob 221 for performing bending operation on the bending portion 212, and a plurality of operating members 222 for performing various types of operation. Moreover, the operating portion 22 has a treatment instrument insertion port 223 that communicates with the treatment instrument insertion passage and that is used for inserting treatment instruments into the treatment instrument insertion passage.

The universal cord 23 extends from the operating portion 22. The universal cord 23 includes a plurality of signal cables for transmitting various signals and an optical fiber for transmitting illumination light supplied from the light source device 6.

The connector 24 is provided at the distal end of the universal cord 23. The connector 24 includes first to third connector units 241 to 243 each of which being connected with an ultrasound cable 31, a video cable 41, and an optical fiber cable 61, respectively.

The ultrasound observation apparatus 3 is electrically connected with the ultrasound endoscope 2 via the ultrasound cable 31 (refer to FIG. 1), outputs a pulse signal to the ultrasound endoscope 2 via the ultrasound cable 31, while inputting echo signals from the ultrasound endoscope 2. Then, the ultrasound observation apparatus 3 performs predetermined processing on the echo signal and generates an ultrasound image.

The endoscopic examination apparatus 4 is electrically connected with the ultrasound endoscope 2 via the video cable 41 (refer to FIG. 1), and inputs an image signal from the ultrasound endoscope 2 via the video cable 41. Then, the endoscopic examination apparatus 4 performs predetermined processing on the image signal and generates an endoscopic image.

The display device 5 is formed with liquid crystal, organic electroluminescence (EL), a projector, a cathode ray tube (CRT), or the like, and displays an ultrasound image generated by the ultrasound observation apparatus 3, an endoscopic image generated by the endoscopic examination apparatus 4, or the like.

The light source device 6 is connected with the ultrasound endoscope 2 via the optical fiber cable 61 (refer to FIG. 1) and supplies illumination light for illuminating portions inside the subject, to the ultrasound endoscope 2 via the optical fiber cable 61.

Figure 3:
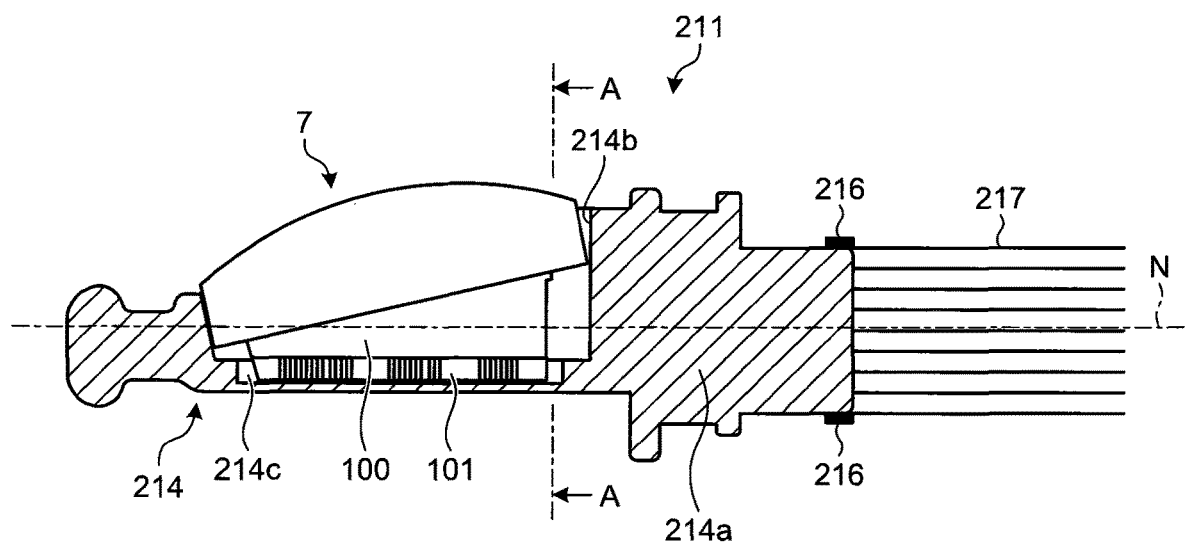
FIG. 3 is a partial cross-sectional view schematically illustrating a configuration of an ultrasound transducer module according to the first embodiment of the disclosure.
Figure 4:
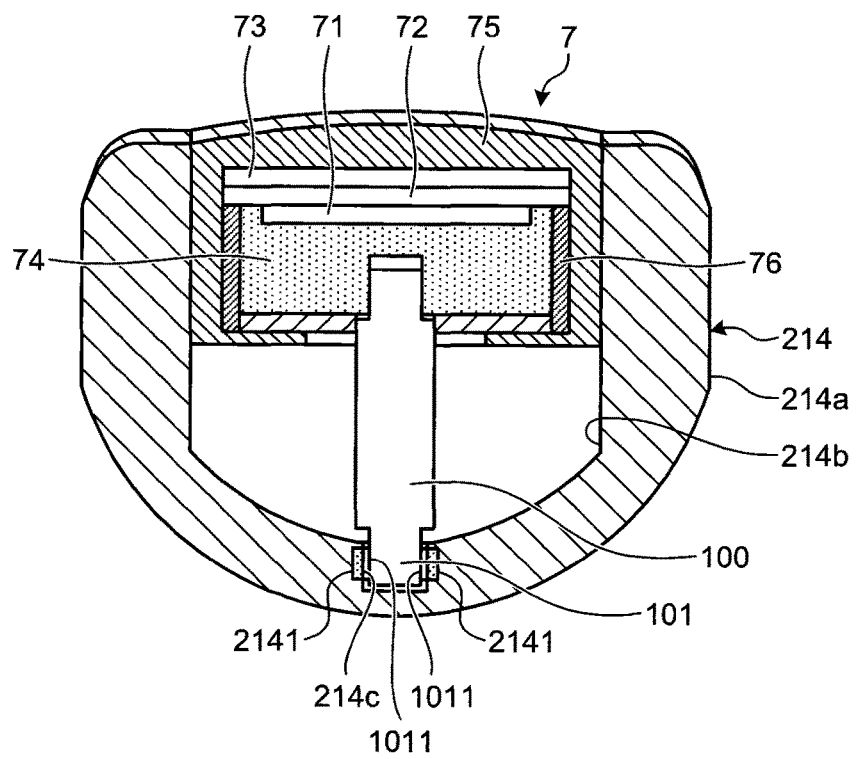
FIG. 4 is a cross-sectional view corresponding to line A-A illustrated in FIG. 3.

Subsequently, the configuration of the ultrasound transducer 7 provided at the distal end of the insertion portion 21 will be described with reference to FIGS. 2 to 5. FIG. 3 is a partial cross-sectional view schematically illustrating the configuration of the ultrasound transducer module according to the first embodiment, including a plane passing through the longitudinal axis N of the insertion portion 21 as a cross-sectional plane. FIG. 4 is a cross-sectional view corresponding to line A-A illustrated in FIG. 3. The first embodiment is described as a case where the ultrasound transducer 7 is a convex type ultrasound transducer including a one-dimensional array (1D array) having a plurality of piezoelectric elements 71 being arranged in a line, as illustrated in FIG. 2. In other words, in the ultrasound transducer 7 according to the first embodiment, the plurality of piezoelectric elements 71 are arranged along an outer surface forming the curved surface of the ultrasound transducer 7, and transmits and receives ultrasound on a plane that includes the longitudinal axis N and is parallel to the longitudinal axis N.

The ultrasound transducer 7 includes a plurality of piezoelectric elements 71, a plurality of first acoustic matching layers 72, a second acoustic matching layer 73, a backing material 74, and an acoustic lens 75 (refer to FIG. 4). Each of the plurality of piezoelectric elements 71 has a prismatic shape and aligned in the longitudinal direction. The plurality of first acoustic matching layers 72 are arranged on the outer surface side of the ultrasound transducer 7 with respect to the piezoelectric element 71. The second acoustic matching layer 73 is provided on the side, opposite to the side coming in contact with the piezoelectric element 71, of the first acoustic matching layers 72. The backing material 74 is provided on the side, opposite to the side coming in contact with the first acoustic matching layer 72, of the piezoelectric element 71. The acoustic lens 75 is provided on the side opposite to the side coming in contact with the first acoustic matching layer 72, on the second acoustic matching layer 73. The acoustic lens 75 is provided on the side, opposite to the side coming in contact with the first acoustic matching layer 72, of the second acoustic matching layer 73. The acoustic lens 75 covers the outer surfaces of the first acoustic matching layer 72, the second acoustic matching layer 73, and a wall portion 76. The acoustic lens 75 forms the outer surface of the ultrasound transducer 7.

The piezoelectric element 71 converts an electrical pulse signal into an ultrasound pulse (acoustic pulse), emits the ultrasound pulse to the subject, converts an ultrasound echo reflected on the subject into an electrical echo signal represented by a voltage change, and outputs the echo signal.

In order to allow the sound (ultrasound) to be efficiently transmitted between the piezoelectric element 71 and the observation target, the first acoustic matching layer 72 and the second acoustic matching layer 73 perform matching of acoustic impedance between the piezoelectric element 71 and the observation target. The first acoustic matching layer 72 and the second acoustic matching layer 73 are formed of mutually different materials. Note that while the first embodiment is described a case where there are two acoustic matching layers (first acoustic matching layer 72 and second acoustic matching layer 73), it is also allowable to have one layer or three layers or more, in accordance with characteristics of the piezoelectric element 71 and the observation target.

The backing material 74 attenuates unneeded ultrasound vibration generated by operation of the piezoelectric element 71. The backing material 74 is formed of a material having a high attenuation rate, for example, epoxy resin in which a filler such as alumina and zirconia is dispersed, or formed of a rubber in which the above-described filler is dispersed.

The acoustic lens 75 is formed with silicone, polymethyl pentene, epoxy resin, polyetherimide, or the like. One of the surfaces of the acoustic lens 75 is formed into a protruding or recessed shape, leading to a function of narrowing the ultrasound, thereby emitting the ultrasound that passes through the second acoustic matching layer 73 to the outside, or incorporating an ultrasound echo from the outside. The acoustic lens 75 may be provided optionally, that is, it is allowable to have a configuration without the acoustic lens 75.

The piezoelectric element 71 vibrates with the input of the pulse signal, whereby the above-configured ultrasound transducer 7 emits ultrasound to the observation target via the first acoustic matching layer 72, the second acoustic matching layer 73, and the acoustic lens 75. At this time, the piezoelectric element 71 is configured such that the backing material 74 attenuates unnecessary vibration from the piezoelectric element 71 on the side opposite to the side on which the first acoustic matching layer 72, the second acoustic matching layer 73, and the acoustic lens 75 are arranged. Moreover, the ultrasound reflected from the observation target is transmitted to the piezoelectric element 71 via the first acoustic matching layer 72, the second acoustic matching layer 73, and the acoustic lens 75. The transmitted ultrasound causes the piezoelectric element 71 to vibrate, then, the piezoelectric element 71 converts the vibration into an electrical echo signal, and outputs, as an echo signal, the electrical echo signal to the ultrasound observation apparatus 3 via wiring (not illustrated).

As illustrated in FIG. 3, the ultrasound transducer module 214 includes a casing 214a. The casing 214a includes an accommodation hole 214b and a fitting hole 214c (holding hole). The accommodation hole 214b is capable of accommodating the above-described ultrasound transducer 7 and a relay substrate 100 described below. The fitting hole 214c is continued to the accommodation hole 214b, and a portion of the relay substrate 100 is to be fitted into the fitting hole 214c. A plurality of electrode pads 216 is provided at an end portion of the casing 214a on the side opposite to the side where the accommodation hole 214b is formed.

The accommodation hole 214b extends in a depth direction, which is a direction orthogonal to the longitudinal axis N, and forms a hollow space capable of accommodating the ultrasound transducer 7 and the relay substrate 100. The "depth direction" as used herein refers to a direction from the opening toward the bottom.

The fitting hole 214c extends in a direction orthogonal to the axial direction of the casing 214a (direction of the longitudinal axis N of the insertion portion 21) from the accommodation hole 214b and has a groove shape into which the portion of the relay substrate 100 can be fitted. The fitting hole 214c includes a plurality of wiring pads 2141 (second wiring pads). The wiring pads 2141 are embedded in the casing 214a, and the surfaces of the wiring pads 2141 on the side that comes in contact with a wiring pad 1011 described below form a portion of the surface of the fitting hole 214c. The electrode pads 216 and the wiring pads 2141 are electrically connected with each other via an FPC substrate (not illustrated) provided inside the casing 214a. Note that the FPC substrate may be a plurality of FPC substrates provided for a plurality of pairs of electrode pads 216 and wiring pads 2141, or may be a single FPC substrate provided for collectively connecting the plurality of pairs of electrode pads 216 and wiring pads 2141. Moreover, it is allowable to configure such that the wiring pads 2141 are embedded inside the casing 214a and the surfaces of the wiring pads 2141 on the side that comes in contact with the wiring pad 1011 may have a shape protruding from the wall surface of the fitting hole 214c.

The respective electrode pads 216 is also connected with a cable 217 forming a portion of a path for electrically connecting the ultrasound transducer 7 (ultrasound transducer module 214) with the ultrasound observation apparatus 3.

The ultrasound transducer module 214 includes the relay substrate 100 that relays the electrical connection between the ultrasound transducer 7 and the cable 217. The relay substrate 100 is a rigid substrate that is held by the ultrasound transducer 7 on one end side of the ultrasound transducer 7, that is, on the side opposite to the surface on which ultrasound is transmitted and received. Moreover, the other end side of the relay substrate 100 includes the wiring pad 1011 (first wiring pad) and a fitting portion 101 that can be fitted into the fitting hole 214c. The fitting portion 101 extends toward the side, opposite to the side held by the ultrasound transducer 7, of the relay substrate 100. In other words, the fitting portion 101 extends in a direction orthogonal to the axial direction of the casing 214a (axial direction of the insertion portion 21) in a state of being accommodated in the accommodation hole 214b. In a state where the fitting portion 101 is fitted into the fitting hole 214c, the corresponding wiring pad 1011 and the wiring pads 2141 come into contact with each other and are electrically connected with each other.

Figure 5:
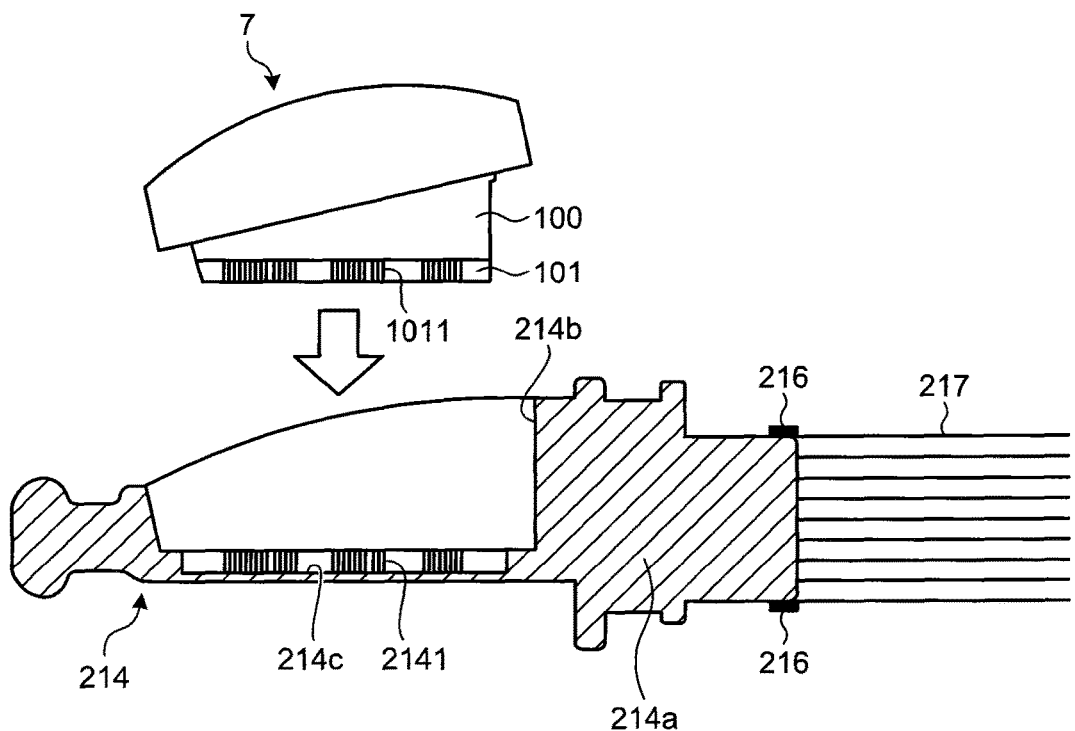
FIG. 5 is a diagram illustrating a method for manufacturing the ultrasound transducer module according to the first embodiment of the disclosure.

Subsequently, a method for manufacturing the above-described ultrasound transducer module 214 will be described with reference to FIG. 5. FIG. 5 is a diagram illustrating a method for manufacturing the ultrasound transducer module according to the first embodiment of the disclosure. In manufacturing the ultrasound transducer module 214, each of cables 217 is connected to each of the electrode pads 216 of the casing 214a.

Thereafter, as illustrated in FIG. 5, the ultrasound transducer module 214 is manufactured by accommodating the ultrasound transducer 7 that holds the relay substrate 100, in the accommodation hole 214b of the casing 214a. When the ultrasound transducer 7 is accommodated in the accommodation hole 214b, the fitting portion 101 of the relay substrate 100 is fitted into the fitting hole 214c at the same time. At this time, the wiring pad 1011 and the wiring pads 2141 come into contact with each other and are electrically connected with each other.

Note that the above-described manufacturing order may be reversed, specifically, it is allowable to first accommodate the ultrasound transducer 7 that holds the relay substrate 100 in the accommodation hole 214b of the casing 214a, and then, connect the cables 217 to the electrode pads 216.

Figure 7:
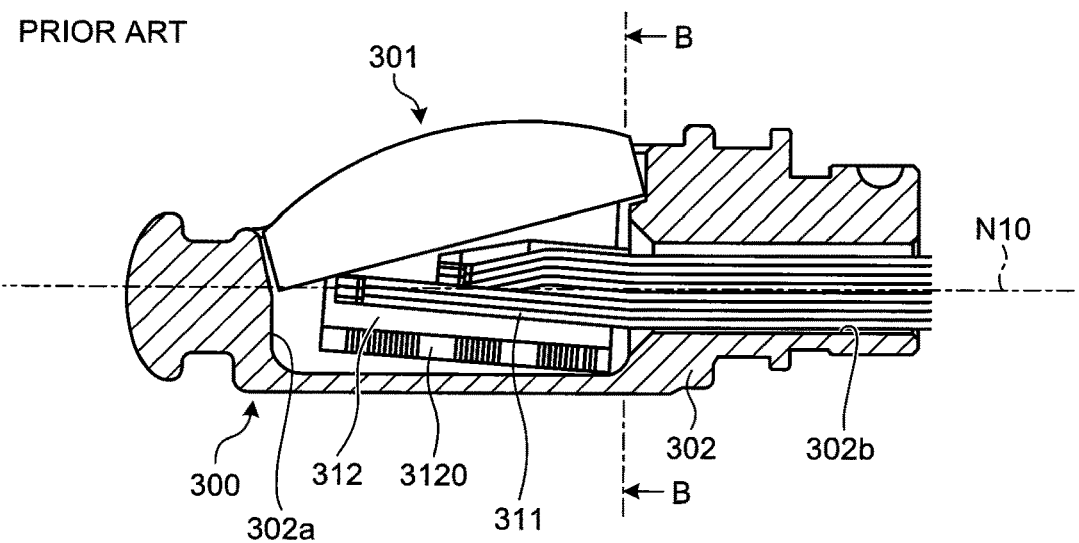
FIG. 7 is a diagram schematically illustrating an exemplary configuration of a distal end portion of an ultrasound endoscope including a conventional convex type ultrasound transducer.
Figure 8:
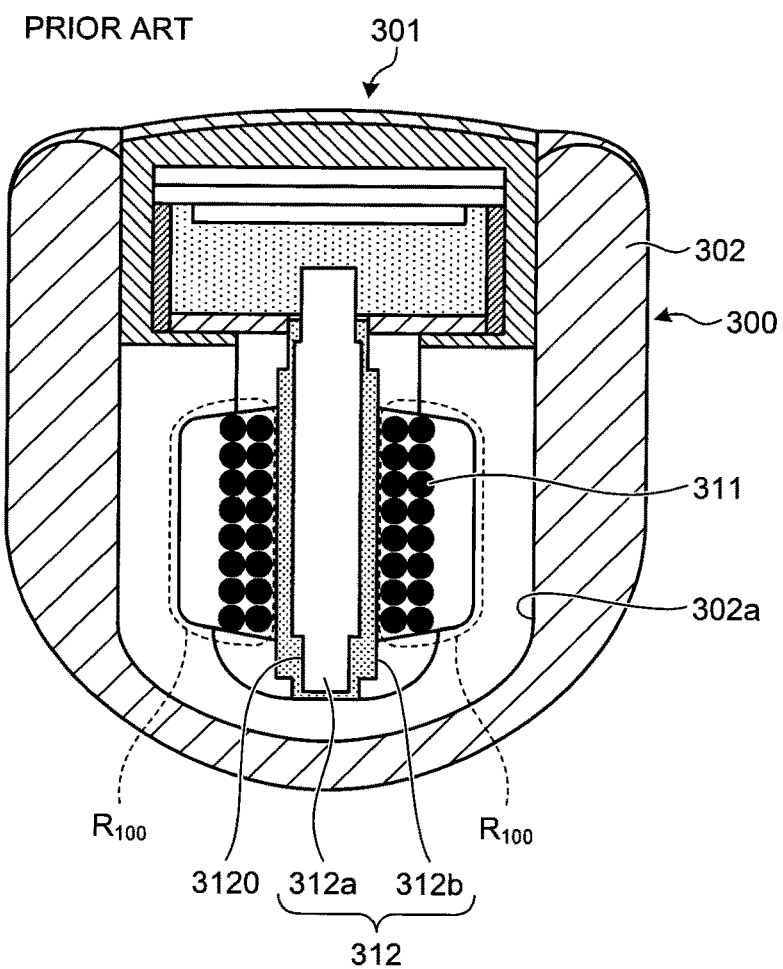
FIG. 8 is a partial cross-sectional view corresponding to line B-B illustrated in FIG. 7.
Figure 9:
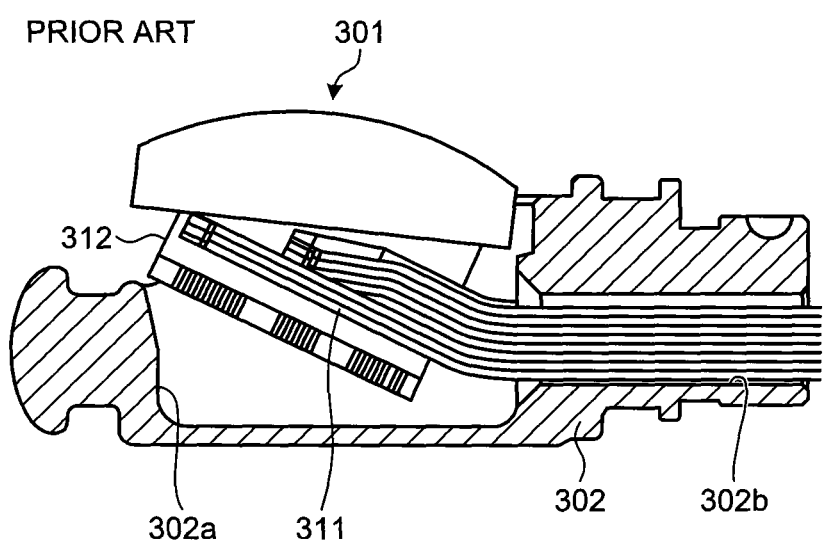
FIG. 9 is a diagram illustrating a portion of a method for manufacturing the ultrasound endoscope including the conventional convex type ultrasound transducer.

According to the first embodiment described above, the relay substrate 100 held by the ultrasound transducer 7 is not directly connected with the cables 217, that is, connected with the cables 217 via the wiring pad 2141s, the internal FPC substrate, and the electrode pads 216. Accordingly, it is possible to have a configuration in which the cables 217 are not inserted into the casing 214a. Accordingly, there is no need to form a space region $R_{100}$ (refer to FIG. 8) for connecting the cable 311 to the relay substrate 312 and no need to form the insertion hole 302b for inserting the cable 311, in the accommodation hole 302a. This makes it possible to reduce the size of the casing 214a of the ultrasound transducer module 214, compared with the casing 302 of the conventional ultrasound transducer module 300 illustrated in FIGS. 7 to 9.

Moreover, in conventional cases, insertion is performed from the cable 311 side to the accommodation hole 302a in a state where the plurality of cables 311 are connected to the relay substrate 312 held by the ultrasound transducer 301. This configuration would bend the cables 311 when the cables 311 come at a portion close to a boundary between the accommodation hole 302a and the insertion hole 302b. This bending of the cables 311 might allow the stress to be applied to a connecting portion between the cables 311 and the relay substrate 312, leading to disconnection, or the like. In contrast, in the configuration according to the first embodiment, the cable 217 is connected to the outside of the casing 214a, without inserting the cables 217 inside the casing 214a when the ultrasound transducer 7 is arranged in the accommodation hole 214b. Accordingly, the above-described problems such as disconnection can be suppressed.

Moreover, in the above-described first embodiment, when the ultrasound transducer 7 is arranged in the accommodation hole 214b, the fitting portion 101 of the relay substrate 100 is fitted into the fitting hole 214c. Accordingly, it is possible to facilitate manufacturing and positioning of the ultrasound transducer 7 with respect to the accommodation hole 214b.

Second Embodiment

Figure 6:
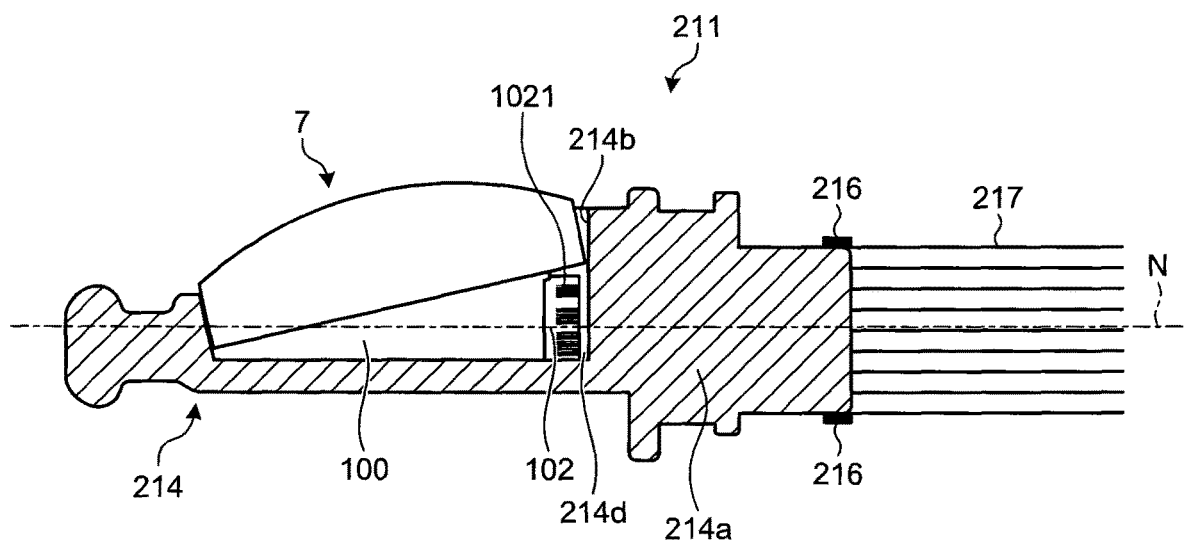
FIG. 6 is a partial cross-sectional view schematically illustrating a configuration of an ultrasound transducer module according to a second embodiment of the disclosure.

FIG. 6 is a partial cross-sectional view schematically illustrating the configuration of the ultrasound transducer module according to a second embodiment, including a plane passing through a longitudinal axis of the insertion portion 21 as a cross-sectional plane. The first embodiment describes a case where the relay substrate 100 is fitted in the direction orthogonal to the axial direction of the casing 214a (axial direction of the insertion portion 21) and the wiring pads 1011 and 2141 are connected with each other. In contrast, the second embodiment is a case where the relay substrate 100 is fitted with the casing 214a in the axial direction of the insertion portion 21 so as to connect the wiring pads with each other.

In the casing 214a according to the second embodiment, a fitting hole 214d is formed instead of the fitting hole 214c according to the above-described first embodiment. The fitting hole 214d extends in the axial direction of the casing 214a (direction of the longitudinal axis N of the insertion portion 21) from the accommodation hole 214b and has a groove shape into which a portion of the relay substrate 100 can be fitted. The fitting hole 214d includes a plurality of wiring pads (second wiring pads, not illustrated) electrically connected with the corresponding electrode pads 216, via the FPC substrate.

Moreover, the relay substrate 100 includes a fitting portion 102 instead of the fitting portion 101 according to the above-described first embodiment. The fitting portion 102 extends in the axial direction of the casing 214a (direction of the longitudinal axis N of the insertion portion 21) in a state of being accommodated in the accommodation hole 214b. The fitting portion 102 includes a plurality of wiring pads 1021 (first wiring pads) that comes in contact with and is electrically connected with the corresponding wiring pads among the plurality of wiring pads formed in the fitting hole 214d.

Also in the second embodiment, the ultrasound transducer module 214 is manufactured by accommodating the ultrasound transducer 7 that holds the relay substrate 100, in the accommodation hole 214b of the casing 214a, similarly to the above-described first embodiment. When the ultrasound transducer 7 is accommodated in the accommodation hole 214b, the fitting portion 102 of the relay substrate 100 is fitted into the fitting hole 214d at the same time. At this time, the wiring pads 1021 and the wiring pads of the fitting hole 214d come into contact with each other and are electrically connected with each other.

According to the second embodiment described above, the relay substrate 100 held by the ultrasound transducer 7 is not directly connected with the cables 217, that is, connected with the cables 217 via the wiring pads of the fitting hole 214d, the internal FPC substrate, and the electrode pads 216, similarly to the case of the first embodiment. Accordingly, it is possible to have a configuration in which the cables 217 are not inserted into the casing 214a. Accordingly, there is no need to form the space region $R_{100}$ (refer to FIG. 8) for connecting the cables 311 to the relay substrate 312 and no need to form the insertion hole 302b for inserting the cables 311, in the accommodation hole 302a. This makes it possible to reduce the size of the casing 214a of the ultrasound transducer module 214, compared with the casing 302 of the conventional ultrasound transducer module 300 illustrated in FIGS. 7 to 9. Even when the space region $R_{100}$ is formed in the casing 214a, it is possible to increase the strength of the casing 214a by filling the space region $R_{100}$ with resin, or the like.

Moreover, according to the second embodiment, the fitting portion 102 extends in the axial direction of the casing 214a (direction of the longitudinal axis N of the insertion portion 21) in a state of being accommodated in the accommodation hole 214b. This leads to reduction of the length in the direction orthogonal to the axial direction of the insertion portion 21, compared with the case of the first embodiment, making it possible to further downsize the distal end configuration of the insertion portion 21.

Embodiments of the disclosure have been described hereinabove, however, the disclosure is not intended to be limited to the above-described embodiments and the modification example. In this manner, the disclosure is not intended to be limited to the above-described embodiments and modification example but may include various forms of embodiments without deviating from the technical spirit and scope of the general inventive concept as defined in the appended claims of this disclosure. Moreover, the components described in each of the embodiments and modification examples may be appropriately combined with each other.

The above-described first and second embodiments describe a case where the fitting portions 101 and 102 of the relay substrate 100 are fitted into the fitting holes 214c and 214d, respectively. It is allowable, however, to configure otherwise as long as the wiring pads come in contact with each other to be electrically connected with each other. For example, it is allowable to configure to allow the wiring pad 2141-side surface of the fitting portion 101 to come in pressure contact with the fitting hole 214c.

In the above-described first and second embodiments, the fitting holes 214c and 214d are formed to have shapes different from those of the accommodation holes 214b. Alternatively, however, when the wiring pads 1011 and 1021 of the relay substrate 100 are provided on the side surfaces, for example, the fitting holes 214c and 214d may constitute a portion of the accommodation hole 214b and the wiring pad (for example, the wiring pad 2141) may be formed at a position corresponding to the wiring pads 1011 and 1021, on the surface of the accommodation hole 214b.

Moreover, while the first and second embodiments describe a case where a piezoelectric element is used for emitting ultrasound and converting ultrasound incident from the outside into echo signals, the disclosure is not limited to this. Specifically, elements using micro electro mechanical systems (MEMS), such as capacitive micromachined ultrasonic transducers (C-MUT) and piezoelectric micromachined ultrasonic transducers (P-MUT) are allowable.

Moreover, the ultrasound endoscope may be applied to a small-diameter ultrasound probe that has no optical system and that performs scanning by mechanically rotating the transducer. In typical cases, the ultrasound probe is inserted into biliary tract, bile duct, pancreatic duct, trachea, bronchus, urethra, and ureter, and is applicable to the observation of the surrounding organs (pancreas, lung, prostate gland, bladder, and lymph nodes, or the like).

Moreover, while an exemplary ultrasound endoscope has been described, the ultrasound transducer module of the disclosure may be applied to an extracorporeal ultrasound probe that emits ultrasound from the body surface of the subject. The external ultrasound probe is typically used to observe abdominal organs (liver, gall bladder, and bladder), breast (mammary gland, in particular), and the thyroid.

As described above, the ultrasound transducer module and the ultrasound endoscope according to the disclosure are useful for downsizing the casing that accommodates the ultrasound transducer.

According to some embodiments, it is possible to reduce the size of the casing that accommodates the ultrasound transducer.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound endoscope comprising:
an insertion portion having a distal end with an ultrasound transducer module, the ultrasound transducer module comprising:
an ultrasound transducer configured to transmit and receive ultrasound;
a substrate electrically connected with the ultrasound transducer, the substrate including a first wiring pad and a connection portion for connecting the substrate to the ultrasound transducer, the first wiring pad and the connection portion being arranged on the substrate at different positions from each other; and
a casing configured to accommodate the ultrasound transducer and the substrate therein, the casing comprising:
an accommodation hole formed in the casing for accommodating the ultrasound transducer and the substrate,
a holding hole by which the substrate is partially held, the holding hole being continuous with the accommodation hole,
a plurality of electrode pads provided on an outer surface of the casing, and
a plurality of second wiring pads provided in the holding hole, each second wiring pad being electrically connected with a corresponding electrode pad among the plurality of electrode pads, and electrically connected with the first wiring pad;
the insertion portion being configured to be inserted into a subject; and
a cable electrically connected to the ultrasound transducer module.

2. The ultrasound endoscope according to claim 1,
wherein the holding hole has a groove configured to partially accommodate the substrate therein, the groove being formed on a surface of the accommodation hole, and
a surface of the second wiring pad, on a side that comes in contact with the first wiring pad, is a portion of a surface of the holding hole.

3. The ultrasound endoscope according to claim 1,
wherein the accommodation hole extends in a direction orthogonal to an axial direction of the casing, the direction being a depth direction of the accommodation hole, and
the holding hole extends from the accommodation hole in a direction perpendicular to the axial direction of the casing.

4. The ultrasound endoscope according to claim 1,
wherein the accommodation hole extends in a direction orthogonal to an axial direction of the casing, the direction being a depth direction of the accommodation hole, and
the holding hole extends from the accommodation hole in the axial direction of the casing.

5. The ultrasound endoscope according to claim 1, wherein the plurality of second wiring pads are electrically connected with the corresponding electrode pad via an internal portion of the casing.

6. The ultrasound endoscope according to claim 1,
wherein the ultrasound transducer is provided at the distal end of the insertion portion to be inserted into the subject, and is configured to transmit and receive the ultrasound on a plane including a longitudinal axis of the insertion portion and parallel to the longitudinal axis,
the substrate is provided on a side opposite to a surface of the ultrasound transducer on which the ultrasound is transmitted and received.

* * * * *